United States Patent [19]

Aumueller et al.

[11] Patent Number: 4,958,022

[45] Date of Patent: Sep. 18, 1990

[54] POLYCYCLIC COMPOUNDS

[75] Inventors: Alexander Aumueller, Deidesheim; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 314,146

[22] Filed: Feb. 23, 1989

[30] Foreign Application Priority Data

Feb. 24, 1988 [DE] Fed. Rep. of Germany ....... 3805758

[51] Int. Cl.$^5$ ................. C07D 251/72; C07D 471/18; C07D 471/22; C07D 487/18
[52] U.S. Cl. ................................. 544/180; 544/215; 544/216
[58] Field of Search ........................ 544/180, 215, 216

[56] References Cited

U.S. PATENT DOCUMENTS 2,345,237 3/1944 Chitwood et al. ................. 260/268
4,769,457 9/1988 Helwig et al. ...................... 544/180

FOREIGN PATENT DOCUMENTS 0213570 8/1986 European Pat. Off. .
0272589 12/1987 European Pat. Off. .
0272591 12/1987 European Pat. Off. .
2300638 1/1973 Fed. Rep. of Germany .
2291203 11/1974 France .
1399561 7/1975 United Kingdom .
1408658 10/1975 United Kingdom .

OTHER PUBLICATIONS

Organic Synthesis Band 64, 1985, Seiten 27–38; S. H. Bertz et al.: "Condensation of Dimethyl 1-3-Acetone—Dicarboxylate with 1,2-Dicarbonyl Compounds: Cis-Bicyclo (3.3.0) Octane -3,7-Diones".

Primary Examiner—John M. Ford
Attorney, Agent, or Firm—Oblon, Spivak, McClelland, Maier & Neustadt

[57] ABSTRACT

Polycyclic compounds of the general formula (I)

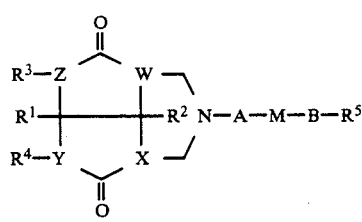

where $R^1$ and $R^2$ independently of one another are each hydrogen, alkyl, cycloalkyl, unsubstituted or substituted phenyl, pyridyl or phenylalkyl, or $R^1$ and $R^2$ together form a trimethylene or tetramethylene group, W, X, Y and Z independently of one another are each C—$R^6$ or nitrogen, one or more of the radicals W, X, Y or Z being C—$R^6$, $R^6$ is hydrogen, —CO$_2$R$^7$, —CONR$^7$R$^8$, cyano or hydroxymethyl and $R^7$ and $R^8$ are each hydrogen, alkyl, unsubstituted or substituted phenyl, cycloalkyl, a 5-membered or 6-membered heterocyclic structure or phenylalkyl, $R^3$ and $R^4$ are each hydrogen or $R^3$ and $R^4$ together form a group of the formula

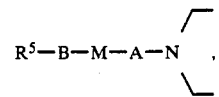

A is a chemical bond, alkylene,

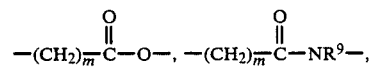

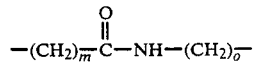

or cycloalkylene, m and o are each from 1 to 20, $R^9$ is alkyl, cycloalkyl, phenylalkyl or unsubstituted or substituted phenyl, M is a group of the formula

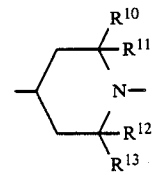

and can be bonded to A both with the nitrogen atom and with the carbon atom, and $R^{10}$, $R^{11}$, $R^{12}$ and $R^{13}$ independently of one another are each alkyl, or $R^{10}$ and $R^{11}$ or $R^{12}$ and $R^{13}$ together form a tetramethylene or pentamethylene group, B is a chemical bond, alkylene or phenylalkylene or is alkylene which is interrupted by carbonyl, carboxamide or a carboxylic ester group, $R^5$ is hydrogen, cyano, hydroxyl,

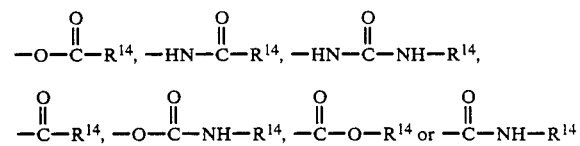

$R^{14}$ is hydrogen, alkyl, cycloalkyl, phenylalkyl, phenyl or a 5-membered or 6-membered heterocyclic structure, or M—B—$R^5$ is a group of the formula (Abstract continued on next page.)

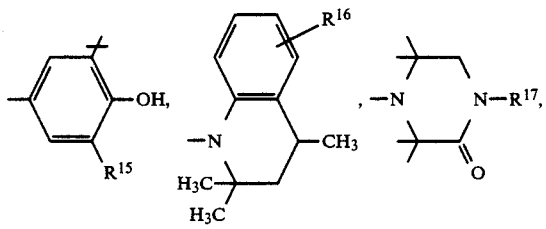
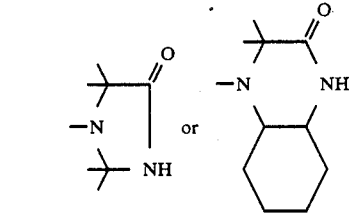
in which case A must not be a chemical bond and $R^{15}$ is alkyl, $R^{16}$ is hydrogen, alkyl or alkoxy and $R^{17}$ is hydrogen or alkyl, have extremely good stabilizing properties and no natural color and are very compatible with organic polymers. They also have a low vapor pressure and are stable to thermal decomposition.
18 Claims, No Drawings

POLYCYCLIC COMPOUNDS

It is known that polyalkylpiperidine derivatives and sterically hindered phenols protect organic polymers from destruction by light and heat.

Polycyclic stabilizers are disclosed in, for example, EP-A No. 213,570.

The unsatisfactory feature of the prior art polycyclic stabilizers is frequently their compatibility with polyolefins and other plastics, the duration of the protective action, their volatility and their thermal decomposition during incorporation into the polymers at elevated temperatures.

It is an object of the present invention to provide novel stabilizers which do not have the above disadvantages.

We have found that this object is achieved by the novel fused heterocycles. The present invention accordingly relates to fused heterocyclic compounds of the general formula I

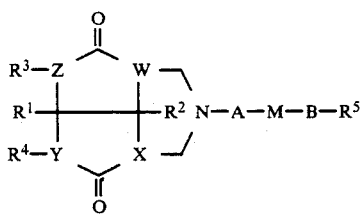

where $R^1$ and $R^2$ independently of one another are each hydrogen, $C_1$-$C_{20}$-alkyl, $C_5$-$C_{12}$-cycloalkyl, unsubstituted or substituted phenyl, pyridyl or $C_7$-$C_{12}$-phenylalkyl, or $R^1$ and $R^2$ together form a trimethylene or tetramethylene group, W, X, Y and Z independently of one another are each C—$R^6$ or nitrogen, one or more of the radicals W, X, Y or Z being C-$R^6$, $R^6$ is hydrogen, -$CO_2R^7$, —$CONR^7R^8$, cyano or hydroxymethyl and $R^7$ and $R^8$ are each hydrogen, $C_1$-$C_{20}$-alkyl, unsubstituted or substituted phenyl, $C_5$-$C_{12}$-cycloalkyl, a 5-membered or 6-membered heterocyclic structure or $C_7$-$C_{12}$-phenylalkyl, $R^3$ and $R^4$ are each hydrogen or $R^3$ and $R^4$ together form a group of the formula

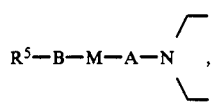

A is a chemical bond, $C_1$-$C_{20}$-alkylene,

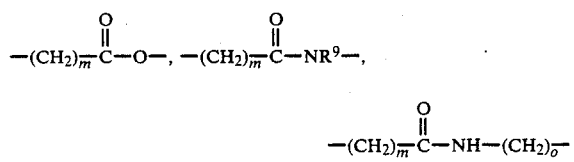

or cycloalkylene, m and o are each from 1 to 20, $R^9$ is $C_1$-$C_{20}$-alkyl, $C_5$-$C_{12}$-cycloalkyl, $C_7C_{12}$-phenylalkyl or unsubstituted or substituted phenyl, M is a group of the formula

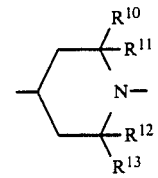

and can be bonded to A both with the nitrogen atom and with the carbon atom, and $R^{10}$, $R^{11}$, $R^{12}$ and $R^{13}$ independently of one another are each $C_1$-$C_4$-alkyl, or $R^{10}$ and $R^{11}$ or $R^{12}$ and $R^{13}$ together form a tetramethylene or pentamethylene group, B is a chemical bond, $C_1$-$C_{20}$-alkylene or $C_7$-$C_{18}$-phenylalkylene or is $C_2$-$C_{20}$-alkylene which is interrupted by carbonyl, carboxamide or a carboxylic ester group, $R^5$ is hydrogen, cyano, hydroxyl,

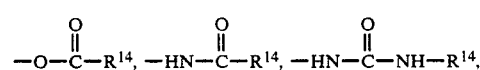

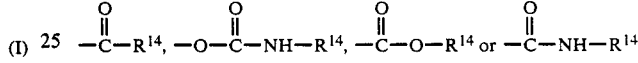

$R^{14}$ is hydrogen, $C_1$-$C_{22}$-alkyl, $C_5$-$C_{12}$-cycloalkyl, $C_5$-$C_{16}$-phenylalkyl, phenyl or a 5-membered or 6-membered heterocyclic structure, or M—B—$R^5$ is a group of the formula

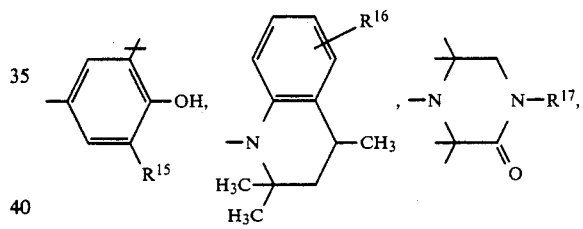

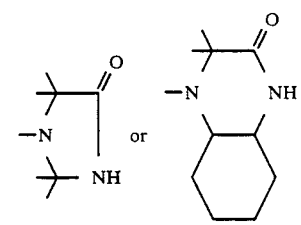

in which case A then cannot be a chemical bond and $R^{15}$ is $C_1$-$C_4$-alkyl, $R^{16}$ is hydrogen, $C_1$-$C_4$-alkyl or $C_1$-$C_4$-alkoxy and $R^{17}$ is hydrogen or $C_1$-$C_{12}$-alkyl.

The novel compounds have extremely good stabilizing properties and no natural color, are very compatible with organic polymers, have a low vapor pressure and are stable to thermal decomposition.

Alkyl radicals $R^1$, $R^2$ and $R^7$ to $R^{17}$ may be straight-chain or branched.

Specific examples of alkyl are methyl, ethyl, propyl, isopropyl, butyl, isobutyl, pentyl, hexyl, lauryl and stearyl.

Examples of cycloalkyl radicals $R^1$, $R^2$, $R^7$, $R^8$, $R^9$ and $R^{14}$ are cyclopentyl, cyclohexyl, cycloheptyl, cyclooctyl and cyclododecyl.

Examples of phenylalkyl radicals $R^1$, $R^2$, $R^7$, $R^8$, $R^9$ and $R^{14}$ are benzyl, methylbenzyl, 2- and 1-phenylethyl, 1-, 2- and 3-phenylpropyl and 1-, 2-, 3- and 4-phenylbutyl.

Suitable unsubstituted or substituted phenyl radicals $R^1$, $R^2$, $R^7$, $R^8$, $R^9$ and $R^{10}$ are phenyl which is unsubstituted or monosubstituted or disubstituted by $C_1$-$C_4$-alkyl, $C_1$-$C_4$-alkoxy, chlorine, N,N-di-$C_1$-$C_4$-alkylamino, $C_1$-$C_4$-alkanoylamino or phenoxy or substituted by methylenedioxy or ethylenedioxy. Specific examples are phenyl, tolyl, ethylphenyl, methoxyphenyl, ethoxyphenyl, chlorophenyl, dimethoxyphenyl, bromophenyl, acetamidophenyl, N,N-dimethylaminophenyl, phenoxyphenyl, N,N-diethylaminophenyl and 3,4-methylenedioxyphenyl.

An example of a heterocyclic radical $R^7$ or $R^8$ is 2,2,6,6-tetramethylpiperidin-4-yl.

$R^1$ and $R^2$ are each preferably hydrogen, methyl, ethyl or phenyl. Compounds of the general formula (I) in which $R^1$ and $R^2$ together form a tetramethylene group are also preferred.

$R^6$ may be, for example,

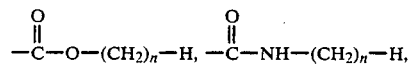

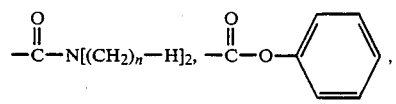

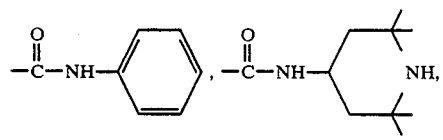

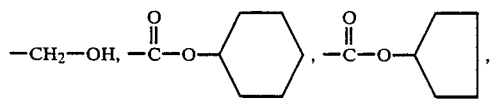

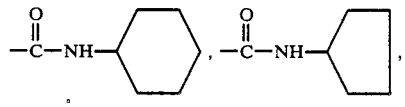

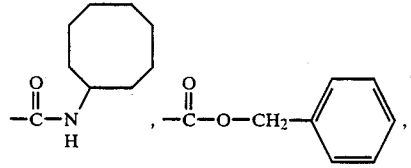

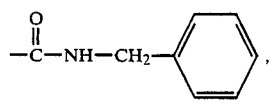

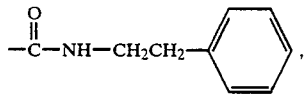

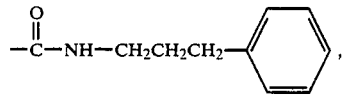

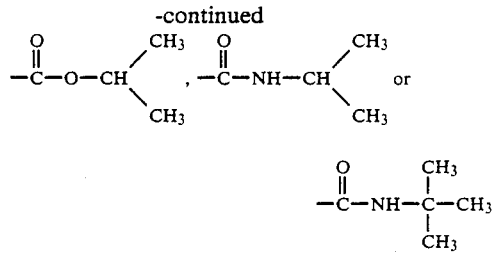

where n is from 0 to 20.

$R^5$ is preferably hydrogen, cyano, —CO—$OCH_3$, —CO—$OCH_2CH_3$ or —CO—$NH_2$.

Examples of bridge members A and B are:

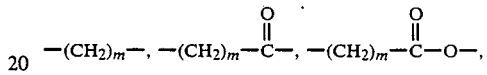

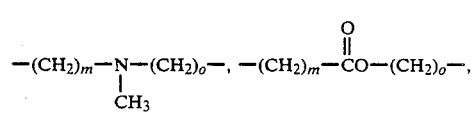

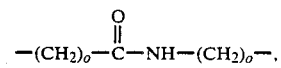

where m and o are each from 1 and 20.

A and B are preferably a chemical bond, —$CH_2$— or —$CH_2$—$CH_2$—.

$R^5$ may be, for example,

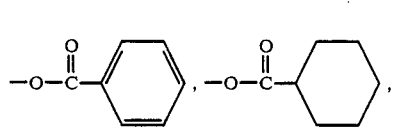

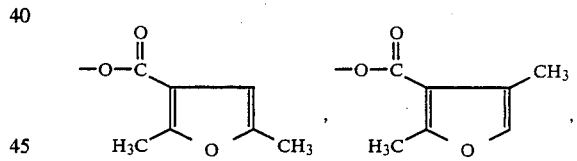

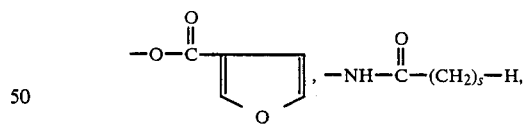

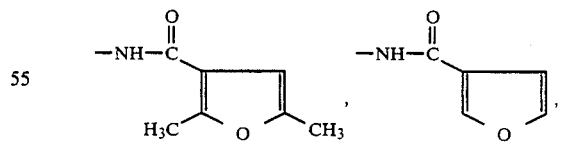

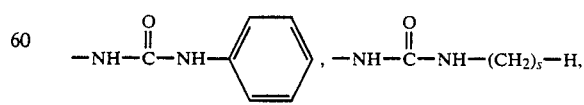

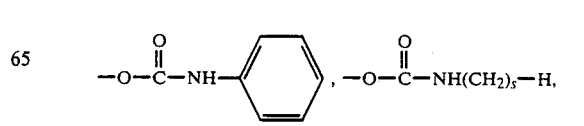

-continued

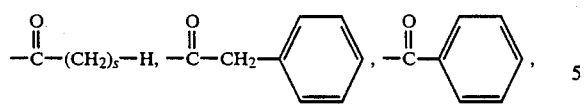

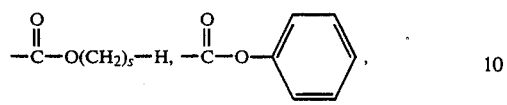

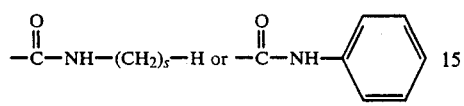

where s is from 1 to 20.

$R^5$ is preferably $C_2$-$C_{18}$-alkanoyloxy or $C_2$-$C_{18}$-alkanoylamino, such as —O—CO—CH₃, —O—CO—CH₂CH₃, —O—CO—(CH₂)₂—CH₃, —o—CO—(CH₂)₃—CH₃, —O—CO—(CH₂)₄—CH₃, —O—CO—(CH₂)₅-CH₃, —O—CO—(CH₂)₅—CH₃, —O—CO—(CH₂)₇—CH₃, —O—CO—(CH₂)₈—CH₃, —O—CO—(CH₂(9)—CH₃, —O—CO-(CH₂)₁₀—CH₃, —O—CO—(CH₂)₁₁—CH₃, —O—CO—(CH₂)₁₂—CH₃, —O—CO—(CH₂)₁₃—CH₃, —O—CO—(CH₂)₁₄—CH₃, —O—CO—(CH₂)₁₅—CH₃, —O—CO—(CH₂)₁₆—CH₃, —NH—CO—CH₃, —NH—CO—CH₂CH₃, —NH—CO—(CH₂)₂—CH₃, —NH—CO—(CH₂)₃—CH₃, —NH—CO—(CH₂)₄—CH₃, —NH—CO—(CH₂)₅—CH₃, —NH—CO—(CH₂)₅—CH₃, —NH—CO—(CH₂)₇—CH₃, —NH—CO—(CH₂)₈—CH₃, —NH—CO—(CH₂)₉—CH₃, —NH—CO—(CH₂)₁₀—CH₃, —NH—CO—(CH₂)₁₁—CH₃, —NH—CO—(CH₂)₁₂—CH₃, —NH—CO—(CH₂)₁₃CH₃, —NH—CO—(CH₂)₁₄—CH₃, —NH—CO—(CH₂)₁₅—CH₃, —NH—CO—(CH₂)₁₆—CH₃ or

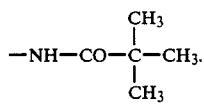

$R^5$ is particularly preferably hydrogen, hydroxyl or cyano.

The group M—B—$R^5$ may furthermore be, for example,

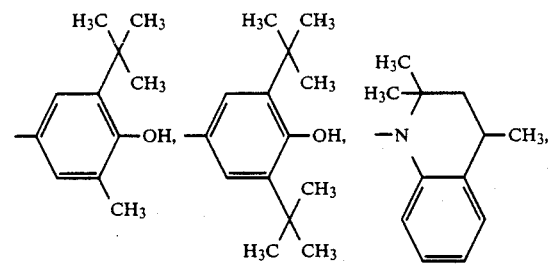

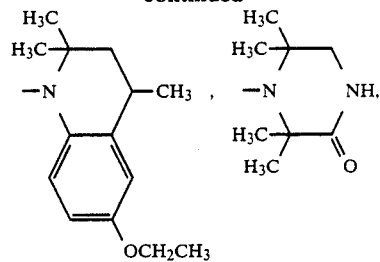

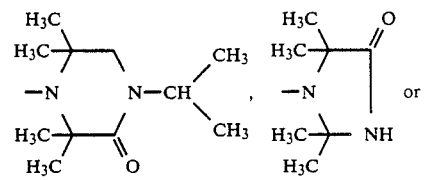

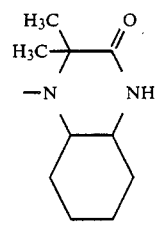

in which case A then cannot be a chemical bond.

The compounds of the general formula (I) can be prepared, for example, by reacting formaldehyde or paraformaldehyde and a bicycle of the general formula (II) with an amine of the general formula (III) or (IV).

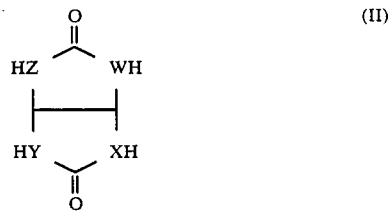

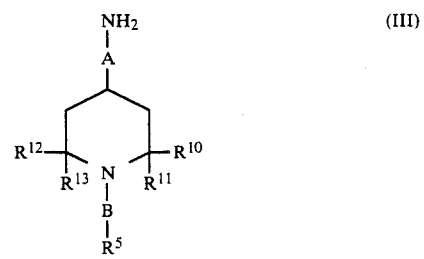

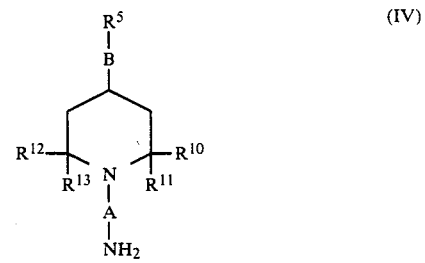

In the formulae, X, Y, Z, W, $R^5$, $R^{10}$ to $R^{13}$, A and B have the abovementioned meanings.

The reaction is preferably carried out in a solvent at from 40° to 120° C., in particular from 60° to 100° C.

Preferred solvents are alcohols, such as methanol, ethanol, propanol, isopropanol, butanol or isobutanol, and water. If mixtures of different amines of the general formulae III and/or IV are used, mixtures of compounds of the general formula (I) are obtained. The two groups A—M—B—R$^5$ which may be present in a molecule can then be identical or different.

Compounds of the general formula (I) which also contain reactive groups, eg. hydroxyl, amino, cyano or an ester group, can be converted into other compounds of the general formula (I) by methods known from the literature, such as acylation, alkylation, reduction, reaction with isocyanates, transesterification or reaction with amines.

Some of the starting materials of the general formula (II) are known (DE-A-2 300 638) and some are novel. The preparation of the novel compounds (II) is described in the Examples.

The novel compounds may be in the form of the free bases, the hydrates or salts. Suitable anions are derived from, for example, inorganic acids and, in particular, organic carboxylic acids and organic sulfonic acids.

Examples of inorganic anions are chloride, bromide, sulfate, methosulfate, tetrafluoborate, phosphate and thiocyanate.

Examples of carboxylic acid anions are formate, acetate, propionate, hexanoate, cyclohexanoate, lactate, stearate, dodecylbenzoate, benzoate, acrylate, methacrylate, citrate, malonate and succinate, and anions of polycarboxylic acids having up to 3,000 COOH groups.

Examples of sulfonic acid anions are benzenesulfonate and tosylate.

The novel compounds (I) stabilize organic material, especially plastics, against degradation by light and heat. They are also effective as metal deactivators. (I) is added to the plastics to be stabilized, in a concentration of from 0.01 to 5, preferably from 0.02 to 2, % by weight, before, during or after polymer formation.

The plastics stabilized by the compounds (I) can, if required, contain further additives, for example antioxidants, light stabilizers, metal deactivators, antistatic agents, flame-retardant agents and pigments and fillers.

The novel compounds (I) can be incorporated by known methods and in the known apparatuses into the plastics to be stabilized, with or without further stabilizers and/or other additives.

Antioxidants and light stabilizers, which can be added to the plastics in addition to the novel compounds, are, for example, compounds based on sterically hindered phenols or sulfur-containing or phosphorus-containing costabilizers.

Examples of such phenolic antioxidants are 2,6-di-tert-butyl-4-methylphenol,n-octadecyl$\beta$-(3,5-di-tertbutyl -4-hydroxyphenyl)-propionate, 1,1,3-tris-(2-methyl4-hydroxy-4-tert-butylphenyl)-butane, 1,3,5-trimethyl2,4,6-tris-(3,,5,-di-tert-butyl-4,-hydroxybenzyl)-benzene, 1,3,5-tris-(3,,5,-di-tert-butyl-4-hydroxybenzyl) isocyanurate, 1,3,5-tris-[$\beta$-(3,,5,-di-tert-butyl-4 '-hydroxyphenyl)-propionyloxyethyl]isocyanurate, 1,3,5-tris-(2,,6,-dimethyl-3,-hydroxy-4,-tert-butylbenzyl) isocyanurate and pentaerythritol tetrakis-[$\beta$-(3,5-ditert -butyl-4-hydro-xyphenyl)-propionate].

Examples of suitable phosphorus-containing antioxidants are tris-(nonylphenyl) phosphite, distearyl pentaerythritol diphosphite, tris-(2,4-di-tert-butylphenyl) phosphite, tris-(2-tert-butyl-4-methylphenyl) phosphite, bis-(2,4-di-tert-butylphenyl) pentaerythritol diphosphite and tetrakis-(2,4-di-tert-butylphenyl) 4,4,' -biphenylene diphosphite.

Examples of sulfur-containing antioxidants are dilauryl thiodipropionate, dimyristyl thiodipropionate, distearyl thiodipropionate, pentaerythritol tetrakis-($\beta$-laurylthiopropionate) and pentaerythritol tetrakis-($\beta$-hexylthiopropionate).

Other antioxidants and light stabilizers which can be used together with the novel compounds (I) are, for example, 2-(2,-hydroxyphenyl)-benzotriazoles, 2-hydroxybenzophenones, aryl esters of hydroxybenzoic acids, $\alpha$-cyanocinnamic acid derivatives, nickel compounds, oxalic acid dianilides and benzimidazolecarboxylic anilides.

Examples of organic polymers which can be stabilized with the novel compounds are: polymers of mono- and diolefins, for example low density or high density polyethylene, linear low density polyethylene, polypropylene, polyisobutylene, polybut-1-ene, polyisoprene and polybutadiene and copolymers of mono- or diolefins or blends of the stated polymers; copolymers of mono- or diolefins with other vinyl monomers, for example ethylene/alkyl acrylate copolymers, ethylene/alkyl methacrylate copolymers, ethylene/vinyl acetate copolymers and ethylene/ acrylic acid copolymers; polystyrene; copolymers of styrene or $\alpha$-methylstyrene with dienes or acrylyl derivatives, for example styrene/butadiene, styrene/acrylonitrile, styrene/ethyl methacrylate, styrene/butadiene/ ethyl acrylate or styrene/acrylonitrile/methyl methacrylate; ABS, MBS and similar polymers; halogen-containing polymers, for example polyvinyl chloride, polyvinyl fluoride, polyvinylidene fluoride and their copolymers; polymers which are derived from $\alpha,\beta$-unsaturated acids and their derivatives, such as polyacrylates and polymethacrylates, polyacrylamides and polyacrylonitriles; polymers which are derived from unsaturated alcohols and amines or their acrylyl derivatives or acetals, such as polyvinyl alcohol or polyvinyl acetate; polyurethanes, polyamides, polyureas, polyesters, polycarbonates, polysulfones, polyethersulfones and polyether ketones.

Furthermore, coatings produced using finishes can be stabilized against degradation by light and heat using the compounds (I). Among these, baking finishes, in particular automotive finishes, preferably two-coat finishes, are particularly noteworthy. In this case too, the abovementioned antioxidants and light stabilizers can be used in addition.

The novel compounds can be added to the finishes in solid or dissolved form. Their good solubility in coating systems is particularly advantageous.

The novel compounds (I) show particularly good stabilizing properties in combination with excellent compatibility in polyolefins, in particular in ethylene polymers and propylene polymers, in polyurethanes and in finishes.

The Examples which follow illustrate the invention.

PREPARATION EXAMPLES

Example 1

11.6 g of 2,8-diazabicyclo[3.3.0]octane-3,7-dione (DE-A-2 300 638), 5 g of paraformaldehyde and 12.9 g of 4-amino-2,2,6,6-tetramethylpiperidine were combined in 80 ml of water and heated for 2 hours at 80° C. The solvent was distilled off under reduced pressure and the residue was recrystallized from acetone. 14.0 g of the compound of the formula

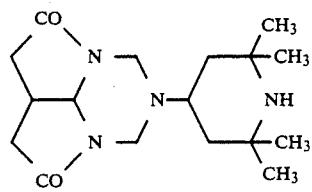

were obtained as a colorless solid of melting point 187° C.

Example 2

18.5 g of methyl 3,7-dihydroxybicyclo[3.3.0]octa 2,6-diene-2,4,6,8-tetracarboxylate (Org. Synth. 64 27) and 6 g of paraformaldehyde in 150 ml of methanol were boiled for 0.5 hour. Thereafter, 15.5 g of -amino-2,2,6,6-tetramethylpiperidine in 150 ml of methanol were added dropwise and the mixture was refluxed for a further hour and poured onto water, and the precipitate which had separated out was filtered off under suction. 4.2 g of the compound of the formula

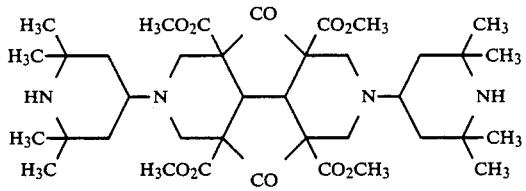

were isolated as a colorless solid of melting point 120°–122°0 C.

By adding catalysts, for example Letatit ® S100, piperidine or pyridine, it was possible roughly to double the yield.

Example 3

20 g of 1,5-dimethyl-3,7-dioxo-2,8-diaza-cisbicyclo[3.3.0]octane-4,6-dicarbonitrile (Chem. Ber. 108 3256), 11 g of paraformaldehyde and 28.5 g of 4-amino-2,2,6,6-tetramethylpiperidine in 250 ml of water were heated at 80° C. for 4 hours. The precipitate which had separated out was filtered off under suction while hot, washed with hot water and dried. 41 g of the compound of the formula

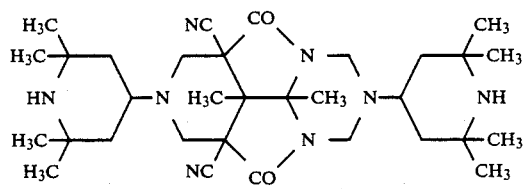

were isolated as a colorless solid of melting point 276° C. decomposition).

The compound contained 0.5 mole of water of crystallization.

Example 4

21.8 g of 1,5-dimethyl-3,7-dioxo-2,6-diaza-cisbicyclo[3.3.0]octane-4,8-dicarbonitrile (Chem. Ber. 108 [1975],3247), 12 g of paraformaldehyde and 31.2 g of 4-amino-2,2,6,6-tetramethylpiperidine in 300 ml of isobutanol were boiled for 4 hours under a water separator. After the mixture had cooled, the product was filtered off under suction, washed with isobutanol and petroleum ether and dried. 50 g of the compound of the formula

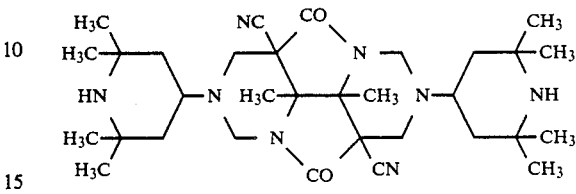

were isolated as a colorless solid of melting point 284° C. (decomposition).

The substance contained 0.5 mole of water of crystallization.

Example 5

51.3 g of a 1 1 mixture of 3,7-dioxo-1,5-diphenyl-2,6-diaza-cis-bicyclo[3.3.0]octane-4,8-dicarbonitrileand3,7-dioxo-1,5-diphenyl-2,8-diaza-cis-bicyclo[3.3.0]octane-4,6-dicarbonitrile (Chem. Ber. 108 [1975], 18 g of paraformaldehyde and 46.8 g of 4-amino2,2,6,6-tetramethylpiperidine in 600 ml of isobutanol were boiled for 3.5 hours under a water separator. The precipitate was filtered off under suction at 70° C. and washed with isobutanol. 64 g of a 1:1 mixture of the compounds of the formulae

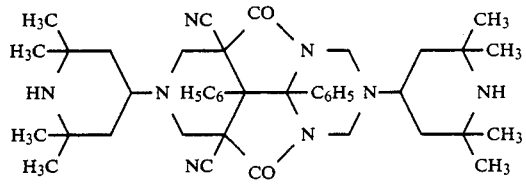

and

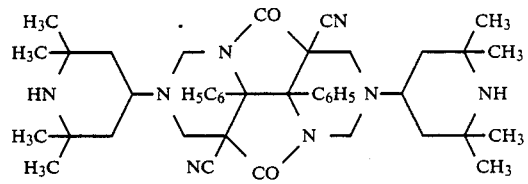

of melting point 278° C. (decomposition) were isolated.

The substance contained 0.5 mole of water of crystallization.

Example 6

A solution of 59.4 g of methyl cyanoacetate in 150 ml of methanol was added dropwise, at 0° C, to 91.2 g of 5-hydroxy-4,5-dimethyl-2-oxo-3-pyrroline-3-carbonitrile (Chem. Ber. 108 [1975], 3262) and 108 g of a 30% strength methanolic sodium methoxide solution. The mixture was left to stand for 18 hours at from 0° to 5° C., 52 ml of concentrated hydrochloric acid were added, stirring was continued for 15 minutes and the mixture was filtered under suction. The residue was heated to the boil in 300 ml of water, the mixture was cooled and filtered under suction and the product was washed with water and dried. 33.2 g of the compound of the formula

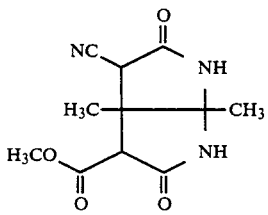

of melting point 262° C. (decomposition) were isolated.

Example 7

15.6 g of 4-amino-2,2,6,6-tetramethylpiperidine were added dropwise to 12.55 g of the product from Example 6 and 6 g of paraformaldehyde in 100 ml of methanol. This gave a solution from which the product was precipitated after the solution had been refluxed for 2.5 hours. The precipitate was filtered off under suction, washed with 100 ml of methanol and dried. 17.7 g of the compound of the formula

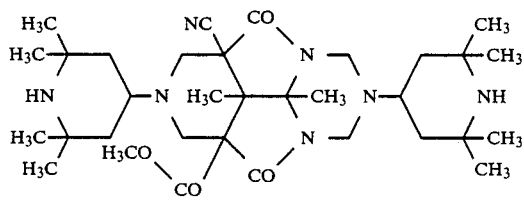

were isolated as a colorless solid of melting point 277° C. (decomposition).

The substance contained 0.5 mole of water of crystallization.

Example 8

11.4 g of the product from Example 6 were heated with 70 ml of 4-amino-2,2,6,6-tetramethylpiperidine at 100° C. for 3 hours and then at 130° C. for 2.5 h ours. A further 50 ml of 4-amino-2,2,6,6-tetramethylpiperidine were added, after which the mixture was kept at 130° C. for a further hour. After the mixture had cooled, 500 ml of petroleum ether were added and the precipitate which had separated out was filtered off under suction, washed with petroleum ether and dried. 14 g of the compound of the formula

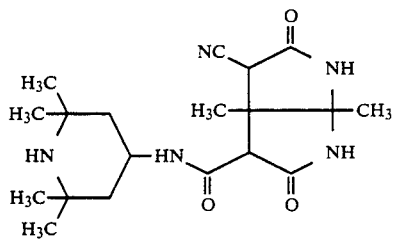

of melting point 262°-263° C. (decomposition) were isolated.

Example 9

10 g of the product from Example 8 were kept with 3.12 g of paraformaldehyde and 8.1 g of 4-amino-2,2,6,6-tetramethylpiperidine in 100 ml of water for 7 hours at 80° C. The precipitate was filtered off under suction at room temperature, washed with water and recrystallized from acetonitrile. 4.5 g of the compound of the formula

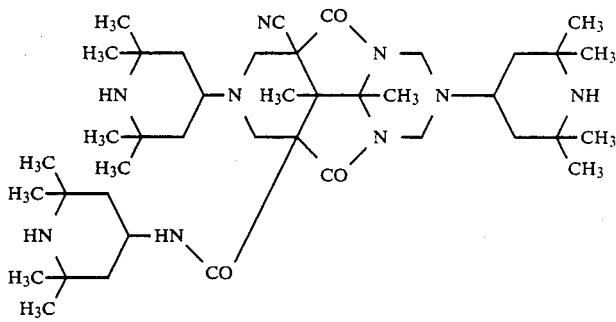

of melting point 291° C. (decomposition) were isolated.

Example 10

91.2 g of 5-hydroxy-4,5-dimethyl-2-oxo-3-pyrroline-3-carbonitrile (Chem. Ber. 108 [1975], 3262) were added to 36 g of urea and 24 ml of concentrated hydrochloric acid in 500 ml of methanol. The mixture was heated for 12 hours at 50° C. and then evaporated down. The oily residue was extracted by boiling with 500 ml of acetone, filtered off under suction while hot, stirred with 150 ml of methanol and 500 ml of acetone, filtered off under suction, washed with acetone and dried. 34.8 g of the compound of the formula

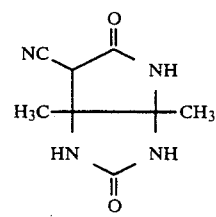

of melting point 274°-275° C. (decomposition) were isolated.

Example 11

5.8 g of the product from Example 10, 3.6 g of paraformaldehyde and 9.3 g of 4-amino-2,2,6,6-tetramethylpiperidine in water were heated at 80° C. for 2 hours.

The precipitate which had separated out was filtered off under suction, extracted by boiling with water, filtered off under suction, washed with water and dried. 11.3 g of the compound of the formula

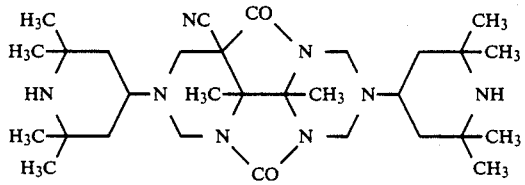

of melting point 277° C. (decomposition) were isolated.

Example 12

(a) 27.6 g of 5-hydroxy-2-oxo-4,5-diphenyl-3-pyrroline-3-carbonitrile (Chem. Ber. 108 [1975], 3262) and 36 g of urea were boiled with 1 g of p-toluene-sulfonic acid in 250 ml of toluene for 30 hours under a water separator. After the mixture had cooled, the product was filtered off under suction, extracted by boiling with water and isopropanol, filtered off under suction, washed with acetone and dried. 20.6 g of the compound of the formula

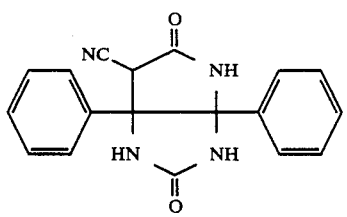

of melting point 297° C. (decomposition) were isolated.

(b) 41.4 g of 5-hydroxy-2-oxy-4,5-diphenyl-3-pyrroline-3-carbonitrile and 180 g of urea were mixed and the mixture was heated to 150° C. After 0.75 hour, the mixture was allowed to cool and 250 ml of water were added dropwise at from 130° to 100° C. At 70° C., the product was filtered off under suction and washed with water. 25 g of a product which was identical to that of Example (a) were isolated.

Example 13

10 g of the product from Example 11 were heated for 5 hours at 80° C. with 3.75 g of paraformaldehyde and 9.8 g of 4-amino-2,2,6,6-tetramethylpiperidine in 300 ml of water. The reaction mixture was filtered off under suction while hot and the residue was recrystallized from dimethylformamide. After the product had been dried, 14 g of the compound of the formula

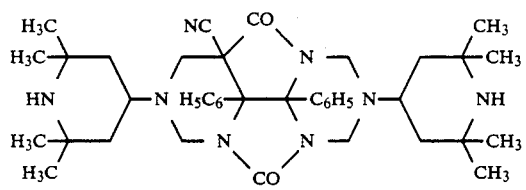

of melting point 300° C. were isolated.

Example 14

134.4 g of cyclohexane-1,2-dione, 100.8 g of cyanoacetamide and 3 ml of piperidine in 1,350 ml of dichloromethane were boiled for 9 hours under a water separator. The reaction mixture was filtered under suction and the residue was washed with petroleun ether and dried. 153 g of the compound of the formula

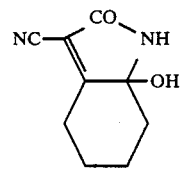

of melting point 169° C. (decomposition) were isolated.

Example 15

13.2 g of malondinitrile in 50 ml of methanol were added dropwise to 35.6 g of the product from Example 14 and 36 g of a 30% strength methanolic sodium methoxide solution in 200 ml of methanol at 0° C. The mixture was stirred for 3 hours at from 0° to 5° C., after which 20 ml of concentrated hydrochloric acid were added dropwise. The precipitate which had separated out was filtered off under suction, washed with petroleum ether, stirred thoroughly with water, filtered off under suction, washed with water and dried. 34 g of the compound of the formula

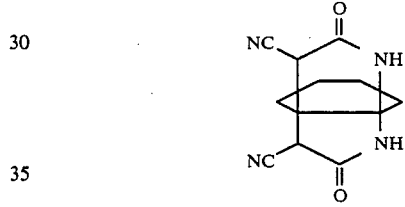

of melting point 289° C. (decomposition) were isolated.

Example 16

10.1 g of the product from Example 15, 5 g of paraformaldehyde and 13.1 g of 4-amino-2,2,6,6-tetramethylpiperidine in 150 ml of water were heated at 80° C. for 2 hours. After the mixture had cooled, the precipitate which had separated out was filtered off under suction, washed with water and recrystallized from acetonitrile. 15 g of the compound of the formula

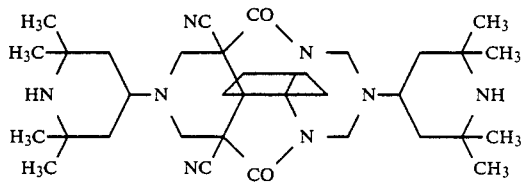

of melting point 279° C. (decomposition) were isolated.

Example 17

14.9 g of methyl cyanoacetate in 40 ml of methanol were added dropwise, at 0° C., to 26.7 g of the product from Example 14 and 27 g of a 30% strength methanolic sodium methoxide solution. The mixture was stirred for 3 hours at from 0° to 5° C. and for 16 hours at room temperature. 16 ml of concentrated hydrochloric acid were added dropwise while cooling with ice, and the precipitate which had separated out was filtered off under suction, washed with methanol, stirred with water, filtered off under suction, washed with water and dried. 16 g of the compound of the formula

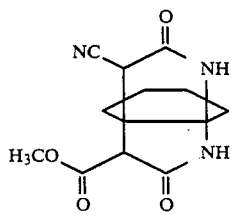

of melting point 262° C. (decomposition) were isolated.

Example 18

12.3 g of the product from Example 17, 5.3 g of paraformaldehyde and 13.7 g of 4-amino-2,2,6,6-tetramethylpiperidine in 150 ml of methanol were refluxed for hours. After the mixture had cooled, the precipitate which had separated out was filtered off under suction, washed with methanol and recrystallized from acetonitrile. 21 g of the compound of the formula

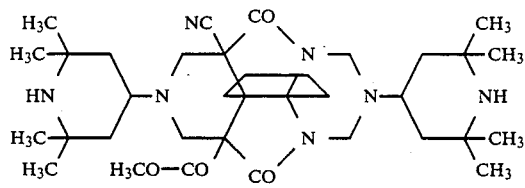

melting point 252° C. (decomposition) were isolated.

Example 19

7.73 g of the product from Example 6, 3.7 g of paraformaldehyde and 9.6 g of 4-amino-2,2,6,6-tetramethylpiperidine were heated at 80° C. for 3.5 hours. The mixture was cooled and then filtered under suction, and the residue was extracted by boiling with 200 ml of water and filtered off under suction. 6.0 g of the compound of the formula

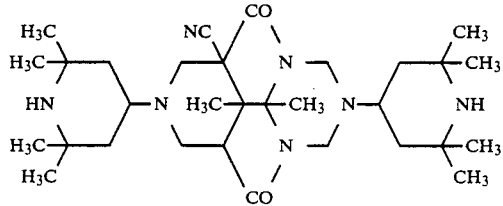

of melting point 299° C. were isolated.

Example 20

120 g of pentane-2,3-dione and 50.4 g of cyanoacetamide in 600 ml of dichloromethane were boiled for 7 hours under a water separator, with the addition of 1 ml of piperidine. The precipitate which had separated out was filtered off under suction and washed with methylene chloride. 57 g of an isomer mixture of the compounds of the formulae

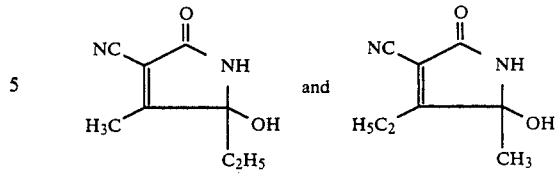

in a ratio of 9:1 ($^{13}$C—NMR) were isolated. The melting point was 157° C. (decomposition).

Example 21

A solution of 6.75 g of malondinitrile in 40 ml of methanol was added dropwise, at 0° C, to a solution of 17 g of the product from Example 20 and 18.4 g of 30% strength methanolic sodium methoxide solution in 100 ml of methanol. The mixture was stirred for 3 hours at from 0° to 5° C. and for 1 hour at room temperature. It was acidified with concentrated hydrochloric acid, and the precipitate which had separated out was filtered off under suction, washed with water and dried at 80° C. 15.0 g of the compound of the formula

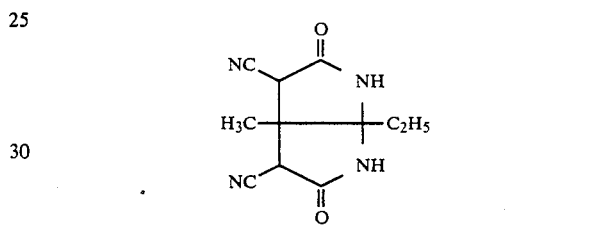

of melting point 266° C. (decomposition) were obtained.

Example 22

12.0 g of the product from Example 21, 20.6 g of 30% strength aqueous formaldehyde solution and 16.1 g of 4-amino-2,2,6,6-tetramethylpiperidine in 150 ml of water were heated at 80° C. for 4.5 hours. The precipitate which had separated out was filtered off under suction while hot, washed with water and recrystallized from acetonitrile. After the product had been dried, 11.0 g of the compound of the formula

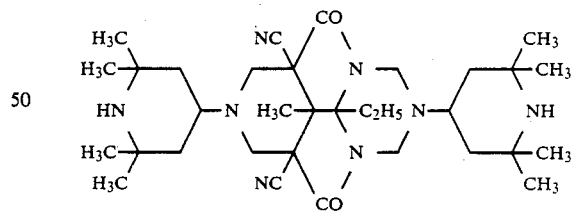

of melting point 292° C. (decomposition) were isolated.

Example 23

10.0 g of 1,5-dimethyl-3,7-dioxo-2,8-diazabicyclo[3.3.0]octane-4-carbonitrile (Chem. Ber. 108 [1975], 3262), 3.1 g of paraformaldehyde and 8.1 g of 4-amino-2,2,6,6-tetra(R)ethylpiperidine in 100 ml of methanol were boiled for 12 hours. After the addition of a further 6.2 g of paraformaldehyde and 16.2 g of 4-amino-2,2,6,6-tetramethylpiperidine, the mixture was boiled for a further hour. The volatile components were removed under reduced pressure from a water pump, the residue was dissolved in toluene at elevated temperatures and the solution was added dropwise to 1 1 of n-hexane. The slowly crystallizing precipitate was filtered off under suction at −20° C., extracted by boiling with n-heptane and dried. 13.3 g of the compound of the formula

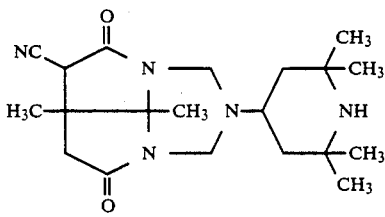

of melting point 172°–173° C. were isolated.

Example 24

9.0 g of 5-methyl-3,7-dioxo-1-phenyl-2,8-diazacis-bicyclo[3.3.0]octane-4,6-dicarbonitrile (Chem. Ber. 5], 3262), 12.8 g of 30% strength aqueous formaldehyde solution and 10.0 g of 4-amino-2,2,6,6-tetramethylpiperidine in 125 ml of water were heated at 80° C. for 3.5 hours. After the mixture had cooled, the precipitate which had separated out was filtered off under suction and recrystallized from methanol. 10.0 g of the compound of the formula

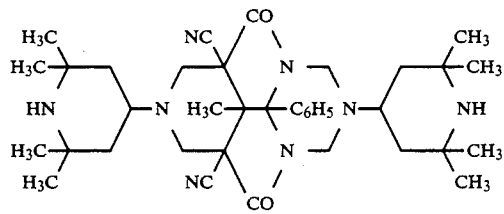

of melting point 295° C. (decomposition) were isolated. The compound contained 0.5 mole of water of crystallization.

Example 25

8.0 g of 5-methyl-3,7-dioxo-1phenyl-2,8-diazacis-bicyclo[3.3.0]octane-4,6-dicarbonitrile (Chem. Ber. 108 [1975], 3262), 11.2 g of 30% strength aqueous formaldehyde solution and 17.5 g of 1-β-aminoethyl-4-hydroxy2,2,6,6-tetramethylpiperidine (German Laid-Open Application DOS No. 3,208,570) in 125 ml of water were heated at 80° C. for 5 hours. After the mixture had cooled, the precipitate which had separated out was filtered off under suction, washed with water and recrystallized from nbutanol. 6.3 g of the compound of the formula

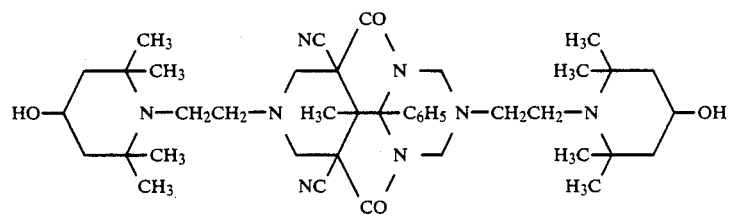

of melting point 239° C. were obtained. The compound contained 0.5 mole of water of crystallization.

Example 26

16.6 g of the product from Example 20 were boiled for 4 hours with 6.6 g of urea and 4 ml of concentrated hydrochloric acid in 100 of methanol, a further 7 g of urea were added and boiling was then continued for 16 hours. The volatile components were removed under reduced pressure from a water pump, the residue was triturated with water and the product was filtered off under suction. Extraction twice by boiling with acetone gave 4.8 g of the compound of the formula

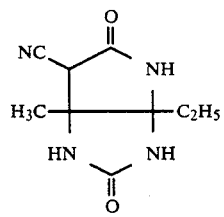

Example 27

4.8 g of the product from Example 26 were heated at 80° C. for 4 hours with 9.2 g of 30% strength aqueous formaldehyde solution and 7.2 g of 4-amino-2,2,6,6-tetramethylpiperidine in 100 ml of water. After the mixture had cooled, the product was filtered off under suction washed with water and recrystallized from acetonitrile and from methanol. 1.7 g of the compound of the formula

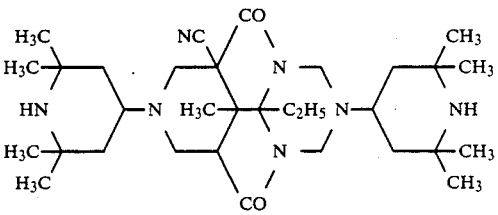

of melting point 284° C. were obtained. The compound contained 0.5 mole of water of crystallization.

Example 28

51.3 g of a 1:1 mixture of 3,7-dioxo-1,5-diphenyl-2,6-diaza-cis-cicyclo [3.3.0]octane-4,8-dicarbonitrile and 3,7-dioxo-1,5-diphenyl-2,8-diaza-cis-bicyclo[3.3.0]octane -4,8-dicarbonitrile (Chem. Ber. 108 [1975], 3262), 16.0 g of 30% aqueous formaldehyde solution and 16.1 g of 1-β-aminoethyl-4-hydroxy-2,2,6,6-tetramethylpiperidine (German Laid-Open Application DOS No. 3,208,570) in 125 ml of water were heated at 80° C. for 2.5 hours. After the mixture had cooled, the product was filtered off under suction and washed with water and the residue was recrystallized from methanol. 15.0 g of a 1:1 mixture of the compounds of the formulae

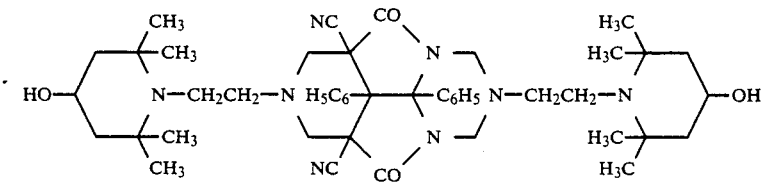

and

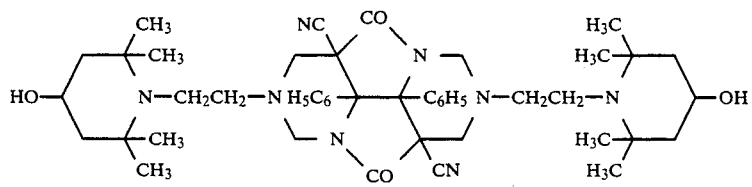

of melting point 247° C. were obtained. The compound contained 1 mole of water of crystallization.

Example 29

27 g of the product from Example 12, 34 g of 30% strength aqueous formaldehyde solution and 36 g of 1-β-aminoethyl-4-hydroxy-2,2,6,6-tetramethylpiperidine (German Laid-Open Application DOS No. 3,208,570) in 300 ml of water and 30 ml of methanol were heated at 80° C. for 2 hours. After the addition of 100 ml of methanol, the mixture was kept at 80° C. for a further 2.5 hours. After the mixture had cooled, the product was filtered off under suction and washed with water and the residue was recrystallized from methanol. 23 g of the compound of the formula

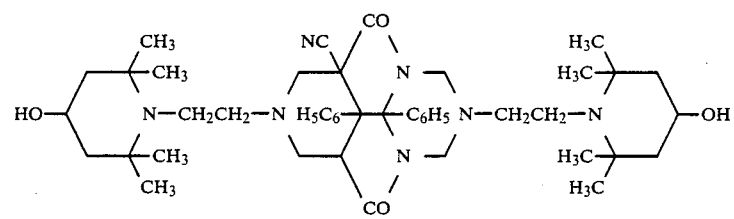

of melting point 247° C. (decomposition) were isolated. The compound contained 0.5 mole of water of crystallization.

Example 30

7.9 g of the product from Example 10, 16.4 g of 30% strength aqueous formaldehyde solution and 17.5 g of 1-β-aminoethyl-4-hydroxy-2,2,6,6-tetramethylpiperidine (German Laid-Open Application DOS No. 3,208,570) in 125 ml of water were heated at 80° C. for 1.5 hours. Thereafter, the mixture was cooled and filtered under suction, and the residue was washed with water and recrystallized from n-butanol. 10.0 g of the compound of the formula

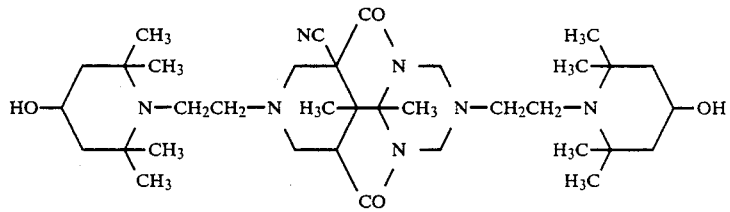

of melting point 280° C. (decomposition) were isolated.

Example 31

10.0 g of the product from Example 6, 4.8 g of paraformaldehyde and 16.1 g of 1-β-aminoethyl-4-hydroxy2,2,6,6-tetramethylpiperidine (German Laid-Open Application DOS No. 3,208,570) in 140 ml of methanol were boiled for 2.75 hours. After the mixture had cooled, the product was filtered off under suction, washed with methanol, recrystallized from acetonitrile and dried to give 13.0 g of the compound of the formula

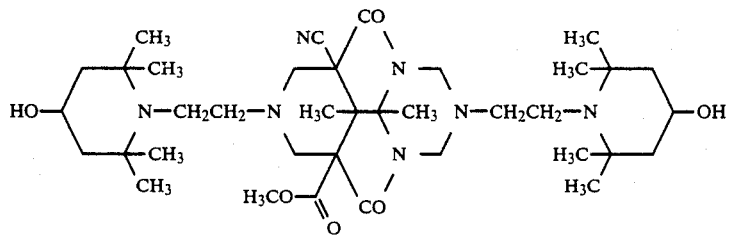

of melting point 254° C. (decomposition).

Example 32

9.6 g of the product from Example 15, 16.0 g of 30% strength aqueous formaldehyde solution and 17.5 g of 1-β-aminoethyl-4-hydroxy-2,2,6,6-tetramethylpiperidine in 125 ml of water and 15 ml of methanol were heated at 80° C. for 5 hours. The mixture was cooled and then filtered off under suction, and the residue was washed with water and extracted by boiling with methanol. 1.8 g of the compound of the formula

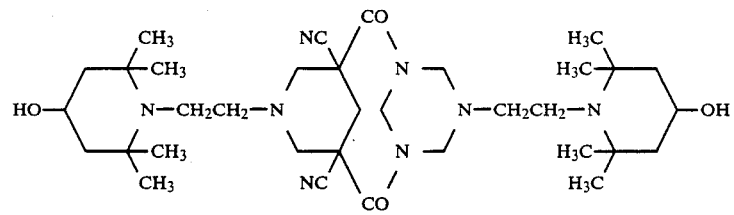

of melting point 271° C. (decomposition) were isolated. The compound contained 0.5 mole of water of crystallization.

Example 33

21 g of the product from Example 30 were introduced into 325 ml of acetyl chloride at from 10° to 20° C. The mixture was stirred for 6 hours at room temperature, after which it was diluted with 250 ml of petroleum ether and filtered under suction. The precipitate was dried and then dissolved in 400 ml of water, and the aqueous solution was filtered and rendered alkaline with 50% strength sodium hydroxide solution, while cooling. The precipitate which had separated out was filtered off under suction, washed with water and dried at 90° C. under reduced pressure from a water pump. 16 g of the compound of the formula

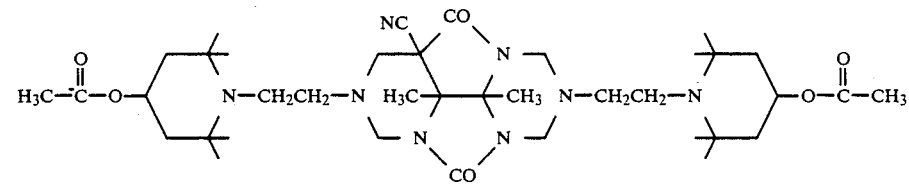

of melting point 242° C. (decomposition) were isolated.

We claim:

1. A polycyclic compound of the formula (I)

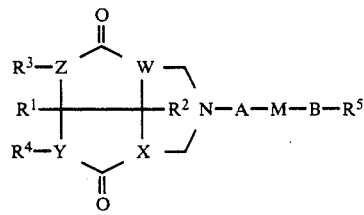

where $R^1$ and $R^2$ independently of one another are each hydrogen, $C_1-C_{20}$-alkyl, $C_5-C_{12}$-cycloalkyl, phenyl which is unsubstituted or monosubstituted or disubstituted by $C_1-C_4$-alkyl, $C_1-C_4$-alkoxy, chlorine, N,N-di- -$C_1-C_4$-alkyl -amino, $C_1-C_4$-alkanoylamino or phenoxy or monosubstituted by methylenedioxy or ethylenedioxy, or pyridyl or $C_7-C_{12}$-phenylalkyl, or $R^1$ and $R^2$ together form a trimethylene or tetramethylene group, W and X are N and Y and Z independently of one another are each C—$R^6$ or nitrogen, one or more of the radicals W, X, Y or Z being C—$R^6$, $R^6$ is hydrogen, —$CO_2R^7$, —$CONR^7R^8$, cyano or hydroxymethyl and $R^7$ and $R^8$ are each hydrogen, $C_1-C_{20}$-alkyl, or phenyl which is unsubstituted or monosubstituted or disubstituted by $C_1-C_4$-alkyl, $C_1-C_4$-alkoxy, chlorine, N,N-di-$C_1-C_4$-alkylamino, $C_1-C_4$-alkanoylamino or phenoxy or monosubstituted by methylenedioxy or ethylenedioxy, or $C_5-C_{12}$-cycloalkyl, 2,2,6,6-tetramethylpiperidin -4-yl or $C_7-C_{12}$-phenylalkyl, $R^3$ and $R^4$ are each hydrogen or $R^3$ and $R^4$ together form a group of the formula

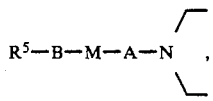

A is a chemical bond, $C_1$-$C_{20}$-alkylene,

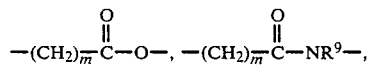

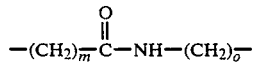

or cycloalkylene, m and o are each from 1 to 20, $R^9$ is $C_1$-$C_{20}$-alkyl, $C_5$-$C_{12}$-cycloalkyl, $C_7$-$C_{12}$-phenylalkyl, phenyl which is unsubstituted or monosubstituted or disubstituted by $C_1$-$C_4$-alkyl, $C_1$-$C_4$-alkoxy, chlorine, N,N-di$C_1$-$C_4$-alkylamino, $C_1$-$C_4$-alkanoylamino or phenoxy or monosubstituted by methylenedioxy or ethylenedioxy, M is a group of the formula

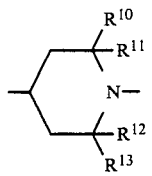

and can be bonded to A both with the nitrogen atom and with the carbon atom, and $R^{10}$, $R^{11}$, $R^{12}$ and $R^{13}$ independently of one another are each $C_1$-$C_4$-alkyl, or $R^{10}$ and $R^{11}$ or $R^{12}$ and $R^{13}$ together form a tetramethylene or pentamethylene group, B is a chemical bond, $C_1$-$C_{20}$-alkylene or $C_7$-$C_{18}$-phenylalkylene or is $C_2$-$C_{20}$-alkylene which is interrupted by carbonyl, carboxamide or a carboxylic ester group, $R^5$ is hydrogen, cyano, hydroxyl,

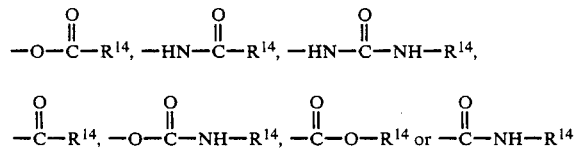

$R^{14}$ is hydrogen, $C_1$-$C_{22}$-alkyl, $C_5$-$C_{12}$-cycloalkyl, $C_5$-$C_{16}$-phenylalkyl or phenyl, or M—B—$R^5$ is a group of the formulae

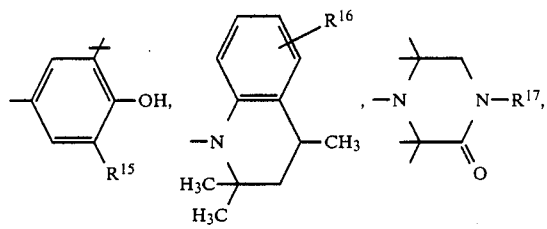

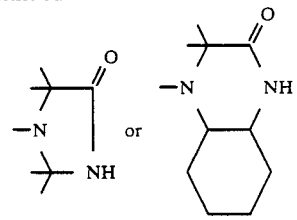

in which case A must not be a chemical bond and $R^{15}$ is $C_1$-$C_4$-alkyl, $R^{16}$ is hydrogen, $C_1$-$C_4$-alkyl or $C_1$-$C_4$-alkoxy and $R^{17}$ is hydrogen or $_1$-$C_{12}$-alkyl.

2. A compound as claimed in claim 1, wherein $R^{10}$, $R^{11}$, $R^{12}$ and $R^{13}$ are each methyl.

3. A compound as claimed in claim 2, wherein $R^1$ and $R^2$ are each hydrogen, methyl, ethyl or phenyl or $R^1$ and $R^2$ together form a tetramethylene group.

4. A compound as claimed in claim 2, wherein $R^6$ is hydrogen, cyano, carbomethoxy, carboethoxy, carbamoyl or N-4-(2,2,6,6-tetramethylpiperidinyl)-carbamoyl.

5. A compound as claimed in claim 3, wherein $R^6$ is hydrogen, cyano, carbomethoxy, carboethoxy, carbamoyl or N-4-(2,2,6,6-tetramethylpiperidinyl)-carbamoyl.

6. A compound as claimed in claim 2, wherein $R^5$ is hydrogen, hydroxyl, cyano, $C_2$-$C_{16}$-alkanoyloxy or $C_2$-$C_{18}$-alkanoylamino.

7. A compound as claimed in claim 3, wherein $R^5$ is hydrogen, hydroxyl, cyano, $C_2$-$C_{18}$-alkanoyloxy or $C_2C_{18}$-alkanoylamino.

8. A compound as claimed in claim 4, wherein $R^5$ is hydrogen, hydroxyl, cyano, $C_2$-$C_{18}$-alkanoyloxy or $C_2$-$C_{18}$-alkanoylamino.

9. A compound as claimed in claim 5, wherein $R^5$ is hydrogen, hydroxyl, cyano, $C_2$-$C_{18}$-alkanoyloxy or $C_2$-$C_{18}$-alkanoylamino.

10. A compound as claimed in claim 2, wherein A and B are each a chemical bond, methylene or ethylene.

11. A compound as claimed in claim 3, wherein A and B are each a chemical bond, methylene or ethylene.

12. A compound as claimed in claim 4, wherein A and B are each a chemical bond, methylene or ethylene.

13. A compound as claimed in claim 5, wherein A and B are each a chemical bond, methylene or ethylene.

14. A compound as claimed in claim 6, wherein A and B are each a chemical bond, methylene or ethylene.

15. A compound as claimed in claim 7, wherein A and B are each a chemical bond, methylene or ethylene.

16. A compound as claimed in claim 8, wherein A and B are each a chemical bond, methylene or ethylene.

17. A compound as claimed in claim 9, wherein A and B are each a chemical bond, methylene or ethylene.

18. A polycyclic compound of the formula (I)

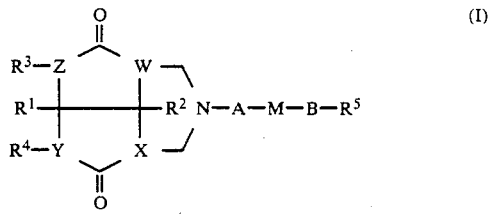

where $R^1$ and $R^2$ independently of one another are each hydrogen, methyl, ethyl or phenyl, or $R^1$ and $R^2$ together form a tetramethylene group, W and X are N and Y and Z independently of one another are each C—$R^5$ or nitrogen, one or more of the radicals Y or Z being $C_z$—$R^6$, $R^6$ is hydrogen, cyano, carbomethoxy, carboethoxy, carbamoyl or N-4-(2,2,6,6-tetramethylpiperidinyl)-carbamoyl, $R^3$ and $R^4$ are each hydrogen or $R^3$ and $R^4$ together form a group of the formula

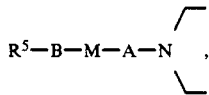

A is a chemical bond, —$CH_2$— or —$CH_2$—$CH_2$—, M is a group of the formula

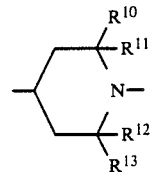

and can be bonded to A both with the nitrogen atom and with the carbon atom, and $R^{10}$, $R^{11}$, $R^{12}$ and $R^{13}$ are each methyl, B is a chemical bond, —$CH_2$— or —$CH_2$—$CH_2$— and $R^5$ is hydrogen, cyano, hydroxyl, $C_2$-$C_{18}$-alkanoyloxy or $C_2$-$C_{18}$-alkanoylamino.

* * * * *